United States Patent
Tepic et al.

(10) Patent No.: US 10,130,481 B2
(45) Date of Patent: Nov. 20, 2018

(54) PATELLAR LIGAMENT SPACER FOR ACL INJURIES

(75) Inventors: Slobodan Tepic, Zürich (CH); Inja Tepic, Zürich (CH)

(73) Assignee: Kyon AG, Zurich (CH)

(*) Notice: Subject to any disclaimer, the term of this patent is extended or adjusted under 35 U.S.C. 154(b) by 349 days.

(21) Appl. No.: 13/877,363

(22) PCT Filed: Nov. 11, 2011

(86) PCT No.: PCT/EP2011/069957
§ 371 (c)(1),
(2), (4) Date: Apr. 2, 2013

(87) PCT Pub. No.: WO2012/062908
PCT Pub. Date: May 18, 2012

(65) Prior Publication Data
US 2013/0190886 A1     Jul. 25, 2013

(30) Foreign Application Priority Data
Nov. 12, 2010 (EP) .................................. 10191075

(51) Int. Cl.
*A61F 2/38*     (2006.01)
*A61B 17/56*     (2006.01)
(Continued)

(52) U.S. Cl.
CPC .............. *A61F 2/389* (2013.01); *A61B 17/56* (2013.01); *A61F 2/08* (2013.01); *A61F 2/3877* (2013.01);
(Continued)

(58) Field of Classification Search
CPC ...... A61F 2/3877; A61F 2/389; A61F 2/4405; A61F 2002/30703; A61F 2230/0095;
(Continued)

(56) References Cited

U.S. PATENT DOCUMENTS 3,872,519 A * 3/1975 Giannestras .......... A61F 2/4202
623/21.18
4,052,753 A     10/1977 Dedo
(Continued)

FOREIGN PATENT DOCUMENTS

WO     2009/018365 A1     2/2009

OTHER PUBLICATIONS

International Search Report issued in International Patent Application No. PCT/EP2011/069957, 4 pages (dated Feb. 6, 2012).
(Continued)

*Primary Examiner* — Andrew Iwamaye
(74) *Attorney, Agent, or Firm* — Rothwell, Figg, Ernst & Manbeck, P.C.

(57) ABSTRACT

A method and implant to treat anterior cruciate ligament (ACL) injuries are disclosed. The method involves advancing the insertion of the patellar ligament to the proximal tibia. The implant includes a spacer (30) which is inserted between the patellar ligament and the tibia and fixed to the tibia. The spacer decreases the angle between the patellar ligament and the tibia plateau and consequently modifies the internal joint force, restoring stability to the joint even if the ACL is ruptured. The method and implants are applicable to both human and canine patients.

7 Claims, 5 Drawing Sheets

(51) Int. Cl.
  *A61F 2/08* (2006.01)
  *A61F 2/30* (2006.01)

(52) U.S. Cl.
  CPC ........... *A61F 2002/30703* (2013.01); *A61F 2220/0008* (2013.01); *A61F 2230/0045* (2013.01); *A61F 2230/0095* (2013.01); *A61F 2250/0081* (2013.01); *A61F 2310/00017* (2013.01); *A61F 2310/00023* (2013.01); *A61F 2310/00029* (2013.01); *A61F 2310/0058* (2013.01); *A61F 2310/00856* (2013.01)

(58) Field of Classification Search
  CPC ...... A61F 2230/0045; A61F 2230/0013; A61F 2230/0032; A61F 2230/0056; A61F 2230/0015; A61F 2230/001; A61F 2002/3031; A61B 17/56; A61B 17/80–17/8095; A61B 17/7001; A61B 17/7002; A61B 17/7008; A61B 17/7032; A61B 17/7043; A61B 17/7044; A61B 17/7047; A61B 17/7049; A61B 17/707
  See application file for complete search history.

(56) References Cited

U.S. PATENT DOCUMENTS

| | | | | | |
|---|---|---|---|---|---|
| 4,431,416 | A | * | 2/1984 | Niznick | A61C 8/0018 433/174 |
| 4,579,529 | A | * | 4/1986 | Urena | A61C 13/225 433/200.1 |
| 4,648,842 | A | * | 3/1987 | Grundei | A61C 8/0012 433/175 |
| 5,053,036 | A | * | 10/1991 | Perren | A61B 17/8052 606/280 |
| 5,151,103 | A | * | 9/1992 | Tepic | A61B 17/8052 606/280 |
| 5,662,652 | A | * | 9/1997 | Schafer | A61B 17/7044 606/261 |
| 5,662,655 | A | * | 9/1997 | Laboureau et al. | 606/75 |
| 5,954,722 | A | * | 9/1999 | Bono | A61B 17/7059 606/281 |
| 6,117,135 | A | * | 9/2000 | Schlapfer | A61B 17/7044 606/250 |
| 6,206,881 | B1 | * | 3/2001 | Frigg | A61B 17/8052 606/291 |
| 6,290,726 | B1 | * | 9/2001 | Pope | A61F 2/30767 623/18.11 |
| 2002/0029045 | A1 | | 3/2002 | Bonutti | |
| 2002/0055744 | A1 | * | 5/2002 | Reiley | A61B 17/15 606/79 |
| 2004/0133281 | A1 | * | 7/2004 | Khandkar | A61F 2/4425 623/17.16 |
| 2004/0162558 | A1 | * | 8/2004 | Hegde | A61B 17/7044 606/287 |
| 2004/0186585 | A1 | * | 9/2004 | Feiwell | A61F 2/4202 623/21.18 |
| 2005/0043803 | A1 | * | 2/2005 | Schultz | A61F 2/4425 623/17.16 |
| 2005/0049711 | A1 | * | 3/2005 | Ball | A61F 2/4202 623/21.18 |
| 2005/0165487 | A1 | * | 7/2005 | Muhanna | A61F 2/4425 623/17.15 |
| 2005/0288792 | A1 | * | 12/2005 | Landes | A61B 17/1682 623/21.18 |
| 2006/0009776 | A1 | * | 1/2006 | Justin | A61B 17/1675 606/87 |
| 2006/0085077 | A1 | * | 4/2006 | Cook | A61B 17/1757 623/17.15 |
| 2006/0116773 | A1 | * | 6/2006 | Cooney, III | A61F 2/4261 623/21.12 |
| 2006/0142870 | A1 | * | 6/2006 | Robinson | A61B 17/15 623/21.18 |
| 2006/0149372 | A1 | * | 7/2006 | Paxson | A61F 2/4425 623/17.11 |
| 2006/0229726 | A1 | * | 10/2006 | Ek | A61B 17/0401 623/17.11 |
| 2006/0229730 | A1 | * | 10/2006 | Railey | A61B 17/15 623/21.18 |
| 2006/0264948 | A1 | * | 11/2006 | Williams | 606/69 |
| 2007/0288021 | A1 | * | 12/2007 | Rickels | A61B 17/1764 606/916 |
| 2009/0018560 | A1 | * | 1/2009 | Mayer | A61F 2/30721 606/151 |
| 2009/0198341 | A1 | * | 8/2009 | Choi | A61F 2/30721 623/21.18 |
| 2010/0004657 | A1 | * | 1/2010 | Dudasik | A61B 17/1757 606/96 |
| 2010/0057216 | A1 | * | 3/2010 | Gannoe | A61F 2/4202 623/21.18 |
| 2010/0121390 | A1 | * | 5/2010 | Kleinman | 606/86 R |
| 2010/0292800 | A1 | * | 11/2010 | Zubok | A61B 17/1604 623/17.16 |
| 2011/0202138 | A1 | * | 8/2011 | Shenoy et al. | 623/20.14 |

OTHER PUBLICATIONS

Written Opinion issued in International Patent Application No. PCT/EP2011/069957, 4 pages (dated Feb. 6, 2012).

* cited by examiner

PATELLAR LIGAMENT SPACER FOR ACL INJURIES

CROSS REFERENCE TO RELATED APPLICATION

This application is a 35 U.S.C. 371 National Phase Entry Application from PCT/EP2011/069957, filed Nov. 11, 2011, which claims the benefit of European Patent Application No. 10191075.0 filed on Nov. 12, 2010, the disclosure of which is incorporated herein in its entirety by reference.

BACKGROUND OF THE INVENTION

Field of the Invention

The invention relates to a method and implants to treat a knee with an injured or ruptured anterior cruciate ligament.

Discussion of Related Art

The Anterior Cruciate Ligament (ACL) in the human knee joint, commonly called Cranial Cruciate Ligament (CrCL) in the canine stifle, is frequently torn in trauma. It also frequently fails, particularly in dogs, after, a degenerative process of still unknown etiology.

In human orthopedics, the standard procedure calls for replacement by an ACL allograft, a part of the patient's own patellar ligament, or a part of the tendon removed from his hamstring muscle. The procedure results in a stable knee, but the long-term performance is often unsatisfactory—75 to 90% of cases result in arthrosis of the joint within 15 years of the procedure.

In dogs, the standard procedure is either an extra capsular suture or one of several geometry modifying surgical techniques. In the extra capsular procedure, a suture is placed outside of the joint, usually on the lateral side, to approximate the function of the ligament. The intention of the suture is to provide stability of the joint for several weeks, while waiting for fibrosis to form around the joint. The fibrosis should provide for long term stability. However, the extra capsular suture technique regularly results in failure. Arthrosis of the joint, at a year or so, is the rule rather exception.

In surgical techniques, the tibia is cut and a segment of it is repositioned to change the geometry in order to stabilize the stifle. Various techniques have been used including: tibial plateau leveling osteotomy (TPLO; Slocum B, Slocum TD; Tibial Plateau Leveling Osteotomy For Repair Of Cranial Cruciate Ligament Rupture In The Canine, Vet. Clin. North Am. 23: 777-795, 1993), cranial closing wedge osteotomy (CWO; Slocum B, Devine T; Cranial Tibial Wedge Osteotomy: A Technique For Eliminating Cranial Tibial Thrust In Cranial Cruciate Ligament Repair, J. Am. Vet. Med. Assoc. 184: 564-569, 1984), and tibial tuberosity advancement (TTA; Tepic S, Damur D M, Montavon P M; Biomechanics Of The Stifle Joint, in Proceedings of the 1st World Orthopaedic Vet. Congress, Munich, Germany, September 2002, pp 189-190). These are significantly invasive procedures which change the overall geometry of the stifle. Of the surgical approaches used in dogs, TTA seems to be associated with lesser morbidity and faster recovery, while providing immediate and durable stability to the joint. Nevertheless, complications and progressing arthrosis are common with each of these techniques.

Intra-articular prostheses are also occasionally used. Again, they require significantly invasive procedures to insert them within the stifle. Even then, they generally end up in failure.

SUMMARY OF THE INVENTION

This invention provides a solution for a minimally invasive stabilization of a knee joint, in dog and in human, by cranially (anteriorly) advancing the patellar ligament just proximally to its insertion to the tibia. According to one aspect of the invention, a spacer is configured to be placed between the distal section of the patellar ligament and the tibia. The spacer is sized and shaped to alter the orientation of the patellar ligament by a pre determined amount. The alteration stabilizes the knee joint which has been weakened by an ACL (or CrCL) failure. According to another aspect of the invention, the spacer may be made from an artificial material, e.g. metal (titanium, stainless steel or a cobalt chromium alloy) or polymer (PEEK, UHMWPE), or from bone (autograft or allograft). According to another aspect of the invention, the spacer is fixed to the tibia body by either conventional screw(s) or an anchor screw, similar to those used for dental implants. According to another aspect of the invention, the surface of the spacer facing the patellar ligament is smooth and exhibits low friction. The material for the spacer should be biocompatible and resistant to wear.

According to another aspect of the invention, the surface of the spacer facing the patellar ligament is engineered so as to provide best conditions for bony ongrowth. For example, a titanium spacer can be anodized, particularly by a process known as Biocer®, or plasma sprayed by either a bone-conductive ceramic or titanium.

According to another aspect of the invention, the spacer is configured to alter the angle of the patellar ligament relative to the tibial plateau. According to one aspect of the invention, the angle is decreased by between 5 and 15 degrees for dogs. According to another aspect of the invention, the angle is decreased by between 10 and 30 degrees in humans. According to another aspect of the invention, the angle of the patellar ligament relative to the tibial plateau is approximately 90 degrees when the knee is extended.

According to another aspect of the invention, a procedure provides stabilization of the knee joint caused by failure of the ACL or CrCL. The procedure includes moving the patellar ligament away from the tibia just above the tibial insertion. A spacer is inserted between the patellar ligament and the tibia and fixed to the tibia. According to another aspect of the invention, the procedure includes altering the angle of the patellar ligament relative to the tibial plateau.

BRIEF DESCRIPTION OF THE DRAWINGS

FIG. 2a is a cross sectional view of the dog knee joint of FIG. 2 through the spacer.

DETAILED DESCRIPTION

Figure 1:
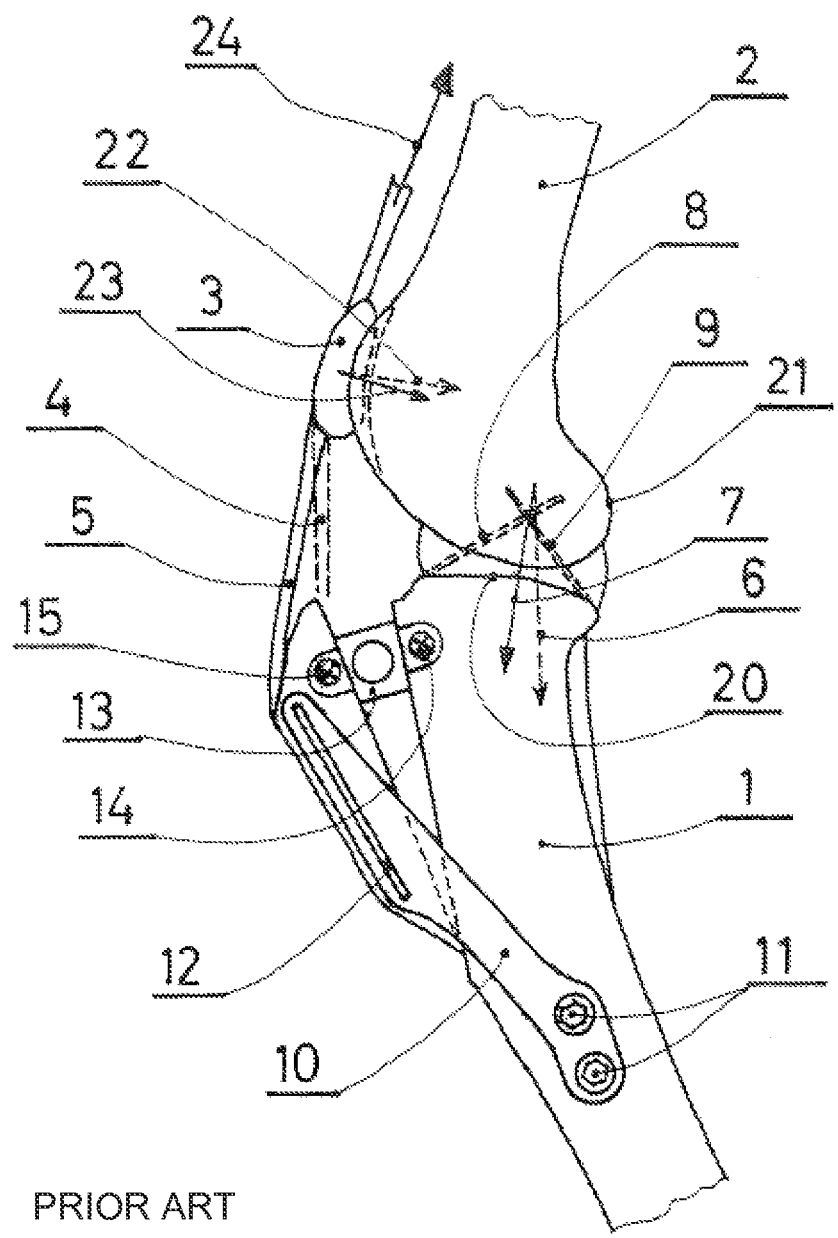
FIG. 1 is a side view of a dog knee joint (stifle) on which the TTA procedure has been performed.

The present invention provides a spacer and a procedure for adjusting the position and angle of the patellar ligament in order to stabilize the knee. The knee is stabilized through geometric changes similar to those achieved by TTA in a much less invasive procedure. The TTA procedure is explained in connection with FIG. 1 to illustrate stabilization of the knee. The TTA procedure is currently accepted as a standard treatment for ruptured ACL in dogs (Fossum T W, Small Animal Surgery, Elsevier Health Sciences, 3$^{rd}$ edition, 2007; Boudrieau R, Tibial Plateau Leveling Osteotomy Or Tibial Tuberosity Advancement?, Vet. Surg. 38:1-22, 2009). FIG. 1 illustrates the knee joint both before and after the TTA procedure. The tibia 1 and the femur 2 articulate at the knee joint via condyles of the femur 21 and condyles of the tibia, also commonly referred to as the tibial plateau 20. Pull 24 from the quadriceps muscles acts on the patella 3, which in turn pulls onto the tibia via patellar ligament 5 (4 in its original orientation). The force between the condyles of the femur and the tibia is approximately parallel to the patellar ligament 5, having been tilted from its original orientation 6 before the advancement (which was parallel to 4) into the new orientation 7, which is perpendicular to the plateau 20. When the joint force 7 is perpendicular to the plateau 20, neither the cranial (anterior) 8, nor the caudal (posterior) cruciate ligament 9 are needed to stabilize the joint. When this condition is satisfied in the extended position of the knee, such as shown on FIG. 1, the joint will also be stable when flexed, stability provided by the caudal (posterior) cruciate ligament.

Advancement of the tuberosity, after an opening wedge osteotomy, is maintained by a cage 13 fixed to the tibia with a posterior screw 14 and an anterior screw 15. The tension of the patellar ligament 5 is transferred to the body of the tibia via a tension-band plate 10, fixed distally to the tibia with screws 11, and proximally to the tuberosity with a fork 12.

In addition to balancing the internal force 7 of the knee joint, TTA also reduces the force 23 (originally 22) between the patella and the femur. A procedure similar to TTA has been invented and performed in human surgery as well by Maquet (Maquet P; Advancement Of The Tibial Tuberosity, Clin. Orthop. Rel. Res. 115: 225-230, 1976).

Figure 2:
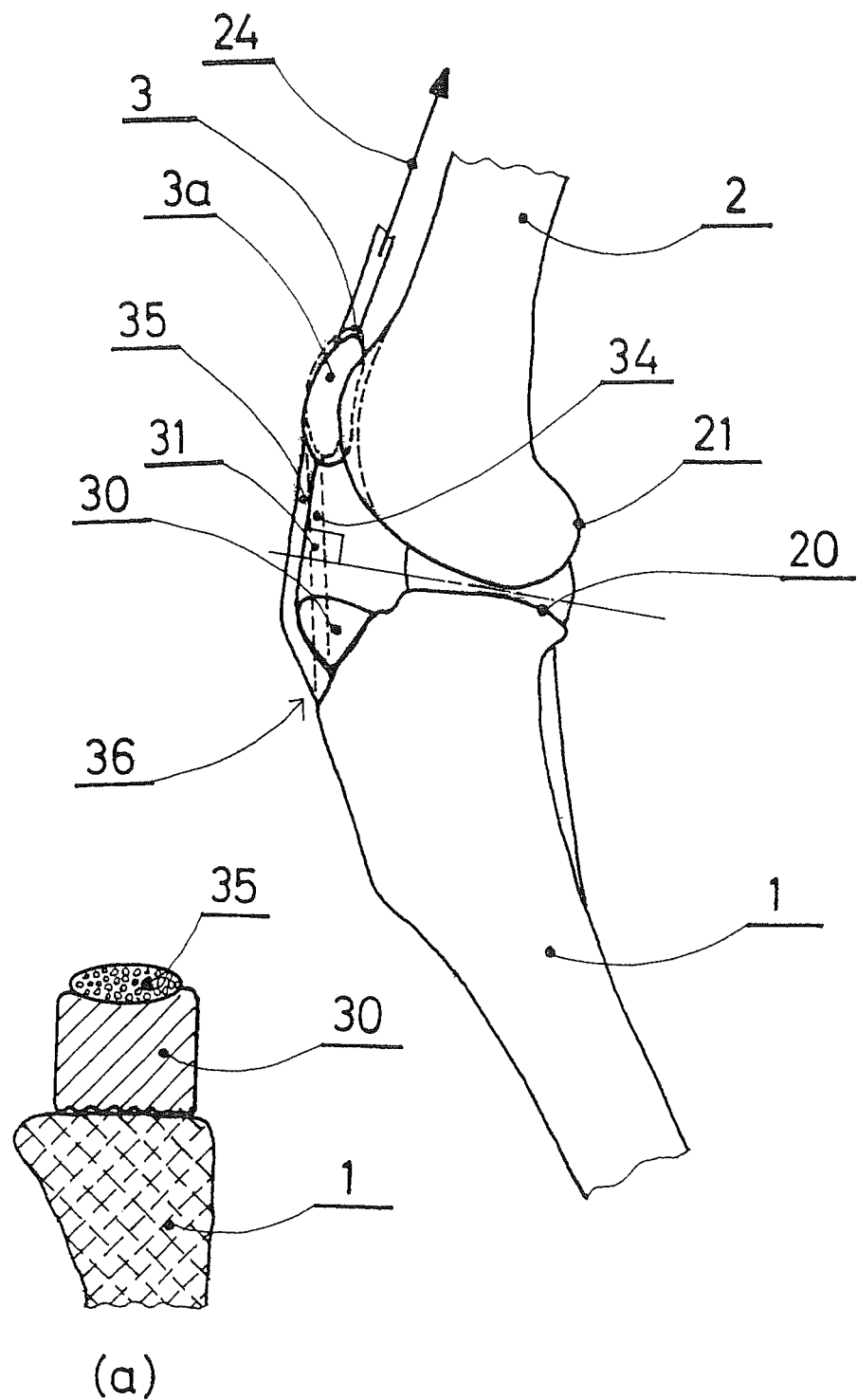
FIG. 2 is a side view of a dog knee joint having a patellar ligament spacer according to an embodiment of the invention.

The procedure of the present invention provides similar changes to those of TTA without the need to cut and reattach the tuberosity. The advantages of the invention are obtained through placement of a spacer between the tibia and the patellar ligament. FIG. 2 shows a medio-lateral view of a dog knee in the extended position with a spacer 30 of the present invention. Patellar ligament has been rotated from its original position 34 to a new position 35 by insertion of a spacer 30 between the patellar ligament and the tibia just proximally to the insertion point 36 of the ligament 35 (34) to the tibia 1. The angle 31 between the patellar ligament 35 and the tibial plateau 20 should be about 90 degrees when the knee is extended to keep the knee stable. In dogs, this calls for an average rotation of the patellar ligament on the order of 5 to 15 degrees; in humans, a larger correction of 10 to 30 degrees is needed for a full compensation of a ruptured ACL. FIG. 2a shows a cross-section through the spacer 30 and the tibia 1. The spacer should preferably be slightly grooved under the ligament so as to keep it in a stable position. This, however, is not an essential requirement—proximity of the insertion should guarantee a stable guidance of the ligament over the spacer.

Under the same pull of the quadriceps 24, the patella 3 will get slightly displaced distally to a new position, marked as 3a. However, this will not affect its function.

Figure 3:
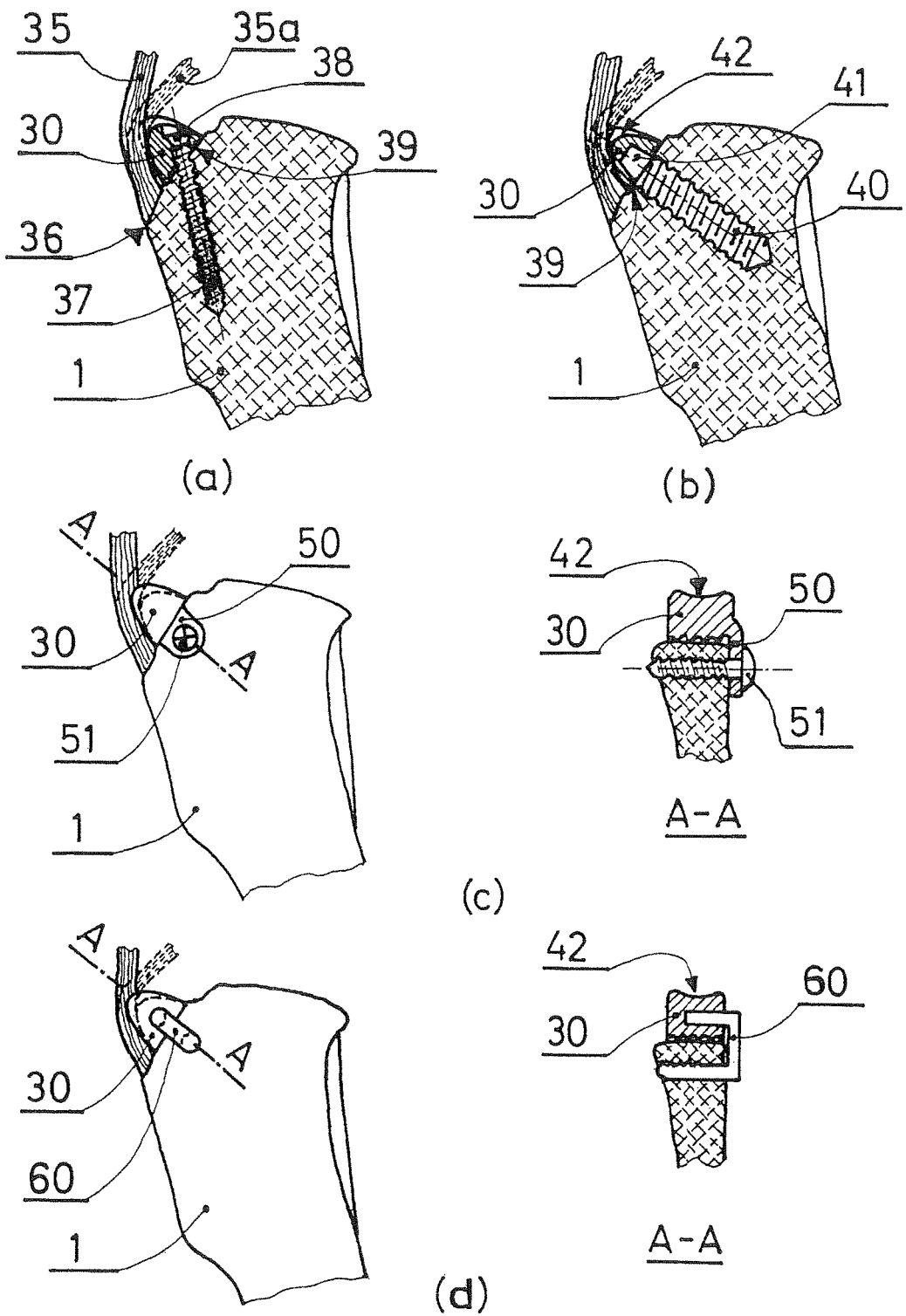
FIGS. 3a-3d illustrate mechanisms for fixing a spacer in a dog knee.

FIG. 3a shows fixation of the spacer 30 to the tibia 1 by means of a bone screw 37, just proximally to the insertion 36 of the ligament 35. The head 38 of the screw 37 should be well countersunk to avoid contact with the patellar ligament 35 which, with flexion, will wrap to a new position marked as 35a. The undersurface 39 facing the tibia bone should preferably be suitable for bony ongrowth or ingrowth.

FIG. 3b shows an alternative method of fixation of the spacer 30 to the tibia 1 by means of an anchor 40. The anchor 40 is screwed into the bone with its conical head 41 left above the level of the bone. The spacer 30 is provided with a matching conical hole. The angle of the conical head and the hole should preferably be self-locking, e.g. 1:10 or 1:20. The bone facing surface 39 of the spacer 30 should preferably be suitable for bony ongrowth or ingrowth.

FIG. 3c shows yet another method of fixation of the spacer 30 to the tibia 1 by means of at least one flange 50, which allows placement of a transverse screw 51 from the medial aspect of the tibia. A second flange could be fixed from the lateral side.

Yet another method of fixation of the spacer 30 is shown on FIG. 3d using a staple-shaped fixation device 60.

The surface 42 of the spacer 30 facing the ligament should be highly polished and resistant to wear. Titanium nitride or diamond-like coatings are suitable for that purpose.

Figure 4:
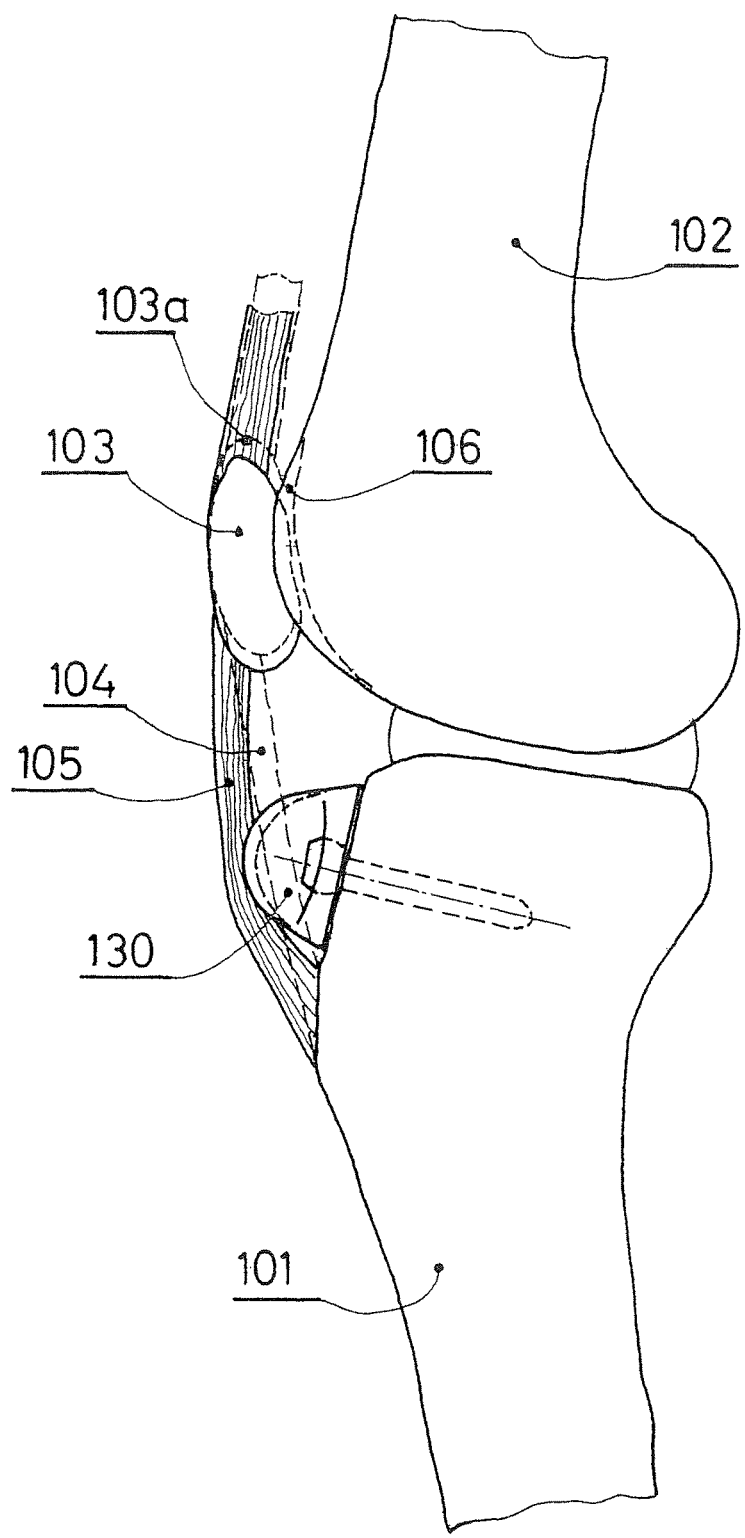
FIG. 4 is a side view of a human knee with a patellar ligament spacer according to an embodiment of the invention.

FIG. 4 shows a saggital view of a human knee with a spacer 130 inserted under the patellar ligament 105 to advance it from its original position 104. The spacer is fixed to the tibia 101. Patella 103 will be slightly displaced distally from its original position, marked as 103a, within the patellar groove 106 of the femur 102.

Figure 5:
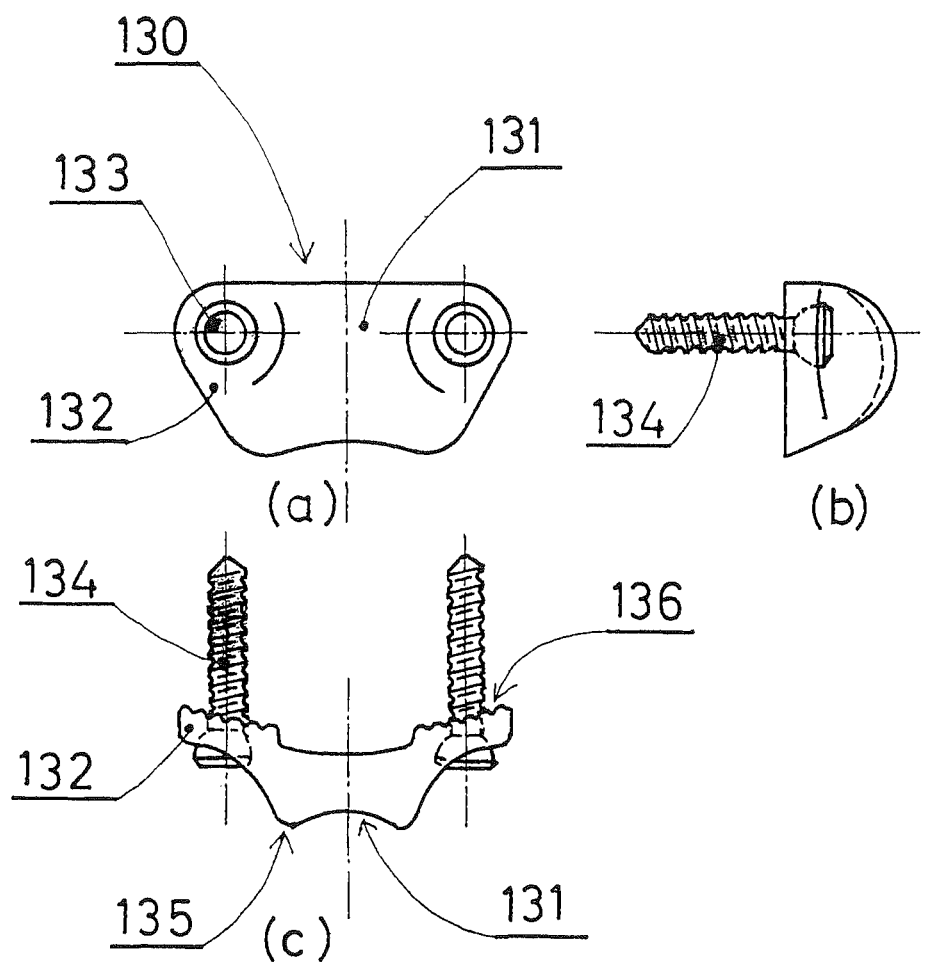
FIGS. 5a-5c are front, side and top views of a spacer for a human knee joint according to an embodiment of the invention.

FIGS. 5a-5c show orthogonal views of an embodiment of a spacer 130 for use in the human knee. The frontal view (FIG. 5a) shows a central section 131 and side sections, or flanges, 132, provided with holes 133 to accommodate bone screws. The top view (FIG. 5c) shows the central section 131 as being grooved, with the ridges 135 intended for guiding the patellar ligament. Side screws 134 can be comfortably placed into the tibial plateau, which in the human knee is much wider than in the dog knee. All of the bone facing surfaces 136 should be well adapted for bony ongrowth or ingrowth, while all of the ligament facing surfaces, e.g. 131 and 135, should be polished and preferably hard-coated for resistance to wear. Alternatively, ligament facing surfaces can be optimized for bony ongrowth—in the final adaptation, the ligament would be sliding over a bone surface.

While the primary indication of the invention is rupture of the ACL in human or CrCL in dog, it can also be used for partial ruptures of the same. It may also be used as a supportive measure for ACL repairs, as well as for intra-articular prosthesis or extra-articular sutures. It can also be used as a substitute for Maquet procedure for patello-femoral joint arthrosis.

Spacers produced from artificial, biocompatible materials have advantages in terms of convenience of use and selection of sizes, but a surgeon could also use a piece of bone, autograft or allograft, appropriately shaped and fixed to the tibia to achieve the same result.

The procedure of the present invention includes advancing the orientation of the patellar ligament to alter the relative angle with the tibial plateau. In an embodiment of the invention, the patellar ligament is advanced so that the relative angle with the tibial plateau is approximately 90 degrees when the knee is extended. In another embodiment of the invention, the patellar ligament is advanced so that the angle is decreased in the range of 10 to 30 degrees. In another embodiment of the invention, the patellar ligament is advanced so that the angle is decreased in the range of 5 to 15 degrees for a dog. In another embodiment of the invention, the patellar ligament is advanced so that the angle is decreased in the range of 10 to 30 degrees for a human.

The patellar ligament may be advanced by inserting a spacer between the ligament and the tibia proximal to the insertion point of the ligament. The spacer may be fixed to the tibia.

Having disclosed at least one embodiment of the present invention, various adaptations, modifications, additions, and improvements will be readily apparent to those of ordinary skill in the art. Such adaptations, modifications, additions and improvements are considered part of the invention which is only limited by the several claims attached hereto.

The invention claimed is:

1. A spacer for implantation onto an anterior aspect of a tibia of a knee, and under a patellar ligament proximally to a location where an end of the patellar ligament is attached to the tibia, the spacer comprising:
   a first surface adapted to face the patellar ligament;
   a second surface adapted to face the tibia, wherein the first and second surfaces are directly connected to one another at respective peripheral edges thereof; and
   at least one screw anchor fixation for the tibia,
   wherein the first surface has a concave surface portion and a convex surface portion, wherein the concave surface portion and the convex surface portion intersect each other, such that a groove is formed on a medial portion of the first surface between two ridges;
   wherein the ridges have extending therefrom a respective side flange, each side flange forming opposed, lateral side faces extending between the first and second surfaces, such that one edge of each side face coincides with an edge of the intersecting concave and convex surface portions of the first surface and a different edge of each side face coincides with an edge of the second surface, at least one side flange including a conical blind hole;
   wherein each of the at least one screw anchor fixation comprises a conical head configured to protrude above a surface of the tibia when the screw anchor fixation is screwed into the tibia, and wherein the conical blind hole is configured to receive the conical head and wherein an angle of the conical head and the conical blind hole is self-locking, and
   whereby the spacer is configured to extend anteriorly such that the patellar ligament is held away from the tibia to alter an angle between the patellar ligament and an axis tangent to a tibial plateau of the tibia.

2. The spacer of claim 1, wherein the first surface has a polished finish and the second surface is adapted for bony integration.

3. The spacer of claim 1, wherein the first surface and the second surface are both adapted for bony integration.

4. The spacer of claim 1, wherein the angle between the patellar ligament and the axis tangent to the tibial plateau of the tibia is 90 degrees when the knee is extended.

5. The spacer of claim 1, wherein the spacer is dimensioned so as to decrease the angle between the patellar ligament and the axis tangent to the tibial plateau of the tibia by 5 to 15 degrees in dogs.

6. The spacer of claim 1, wherein the spacer is dimensioned so as to decrease the angle between the patellar ligament and the axis tangent to the tibial plateau of the tibia by 10 to 30 degrees in humans.

7. The spacer of claim 1, comprising at least two screw anchor fixations for the tibia.

* * * * *